United States Patent [19]

Meyer et al.

[11] Patent Number: 4,738,257
[45] Date of Patent: Apr. 19, 1988

[54] OCCLUSIVE WOUND CARE DRESSING

[75] Inventors: Ralph A. Meyer, Round Lake Beach; Wagdi W. Habib, Roselle; James A. Stupar, Crystal Lake, all of Ill.

[73] Assignee: Hollister Incorporated, Libertyville, Ill.

[21] Appl. No.: 907,501

[22] Filed: Sep. 15, 1986

Related U.S. Application Data

[63] Continuation-in-part of Ser. No. 872,803, Jun. 11, 1986, abandoned.

[51] Int. Cl.⁴ ............................................. A61L 15/00
[52] U.S. Cl. .................................................... 128/156
[58] Field of Search ................................. 128/156, 157

[56] References Cited

U.S. PATENT DOCUMENTS

| | | | |
|---|---|---|---|
| 3,972,328 | 8/1976 | Chen | 128/156 |
| 4,202,925 | 5/1980 | Dabroski | 128/156 |
| 4,231,369 | 11/1980 | Sorensen et al. | 604/336 |
| 4,253,460 | 3/1981 | Chen | 128/156 |
| 4,286,592 | 9/1981 | Chadrasekarah | 128/156 |
| 4,477,325 | 10/1984 | Osburn | 264/22 |
| 4,484,574 | 11/1984 | DeRusha | 128/156 |
| 4,516,571 | 5/1985 | Buchan | 128/156 |
| 4,522,997 | 6/1985 | Schmitz | 128/156 |
| 4,538,603 | 9/1985 | Paweichak | 128/156 |

*Primary Examiner*—Gregory E. McNeill
*Attorney, Agent, or Firm*—Tilton, Fallon, Lungmus & Chestnut

[57] ABSTRACT

An occlusive dressing for care of skin wounds includes a skin contacting barrier layer and an overlying backing layer. The backing layer is formed from a thin sheet which is stretchable, and the barrier layer is formed from a composition having an elastomeric phase integrated by a cross-linked polymer network with a particular water-absorbing hydrocolloid phase dispersed therein.

12 Claims, 2 Drawing Sheets

OCCLUSIVE WOUND CARE DRESSING

RELATED APPLICATION

This application is a continuation-in-part of copending applicaiton Ser. No. 872,803, filed June 11, 1986 now abandoned.

FIELD OF INVENTION

This invention relates to occlusive dressings for care of fluid-exuding skin wounds such as particularly pressure sores and dermal ulcers.

BACKGROUND OF INVENTION

The management of pressure sores and dermal ulcers presents hospitals and nursing homes with difficult problems. Such skin wounds occur with high frequency on sedentary patients confined to beds and wheelchairs. The contact of the patient's body with the bed or chair can cause skin irritations and abrasions which develop into painful sores. Vascular insufficiency due to aging and disease contribute to localized tissue ischemia and leads to ulceration of the extremities. Such skin wounds once formed tend to be non-healing, or if healed temporarily, they reoccur. Procedures for both short-term and long-term management of pressure sores and ulcers are therefore needed.

The use of so-called "occlusive" dressings for pressure sores and ulcers has gained increasing acceptance in recent years. A number of wound dressings of this kind are available commercially. Most of these products are formed from several layers, including at least an inner skin-contacting layer and an outer backing layer. The dressing is applied as a cover for the sore or ulcer in a size providing a margin around the wound area which adhesively seals to the skin. The inner layer, commonly referred to as the barrier layer, contains water-absorptive material, such as hydrocolloids, so that fluid from the wound is absorbed into the barrier, making it possible to keep the dressing in place for at least several days. Such occlusive dressings tend to promote healing by maintaining the wound under moist conditions, and serve as a barrier against bacterial infection.

While previously known occlusive dressings have overcome some of the problems associated with the management of pressure sores and dermal ulcers, they have been found to have certain limitations or disadvantages which have not heretofore been overcome. Absorption of fluid by the portion of the barrier layer in contact with the wound causes the central portion of the applied dressing to swell and push against the wound. Continued swelling can induce separation of the barrier from the skin outside of the wound area. Fluid may enter between the inner surface of the barrier and the surrounding skin, working its way outward until it reaches the periphery of the barrier. A primary concern is that such leakage provides a tract for the invasion of pathogenic microorganisms. Also, such leakage can cause skin maceration, leading to enlargement of the wounds.

Leakage of the wound fluid is objectionable because of its unpleasant odor. Further, the dressing must be replaced when leakage develops. The more hydrocolloid included in the barrier layer the greater its fluid-absorbing capacity, but too much absorbency can limit the life of the dressing because of induced leakage.

In the management of pressure sores, it is desirable that the occlusive dressing be removable in one piece. This minimizes the need to cleanse the wound between dressing applications. At the same time, stripping of the central portion of the barrier from the wound can damage healing tissue.

In an effort to ameliorate some of the foregoing difficulties, a wound care product in use in the United States utilizes a barrier layer that loses its integrity after absorbing wound fluid. The portion of the barrier layer in contact with the wound is converted to a gel-like material. When the dressing is removed, this gel material is left in the wound, and must be removed to permit examination and/or before applying another dressing. Effective cleansing has required washing out the gel from the wound with saline solution, which must be carried out carefully and gently to avoid damage to the wound bed and newly-formed tissue. This can be a time-consuming procedure for nursing personnel.

A wound dressing of the decomposing gel-forming type is disclosed in U.S. Pat. No. 4,538,603. This dressing utilizes a three-layer composite, also generally described in prior U.S. Pat. No. 3,972,328. A layer of semi-open cell foam material is interposed between the barrier layer and an outer film layer. The barrier layer contains hydrocolloids. Because of the large amount of hydrocolloid used, the barrier material disintegrates into a non-structural gel on absorbing wound fluid.

Cross-linked barrier material providing improved structural integrity have been described for use in ostomy applications. See, particularly, U.S. Pat. Nos. 4,477,325 and 4,231,369. The latter patent also suggests the possibility of using a cross-linked barrier material in a wound drainage application, viz. around a wound. However, as far as is known, prior to the present invention no one has provided a practical and effective occlusive dressing for pressure sores or dermal ulcers which utilizes a cross-linked barrier material in contact with the wound.

SUMMARY OF INVENTION

The improved occlusive dressing of the present invention comprises an assembly of a barrier layer and a backing layer which cooperate for increasing fluid absorption without inducing dislodgement and leakage, and which facilitates one piece removal with minimal wound irritation. The backing is formed of a thin elastic sheet which is yieldable as the barrier material swells. The hydrocolloid-containing barrier material has a continuous elastomeric phase which is cross-linked to form an integrated network. As the portion of the barrier over the wound area takes up fluid, it swells with relatively little restraint, the overlying portion of the backing stretching upwardly as the central portion of the barrier enlarges. At the same time, the marginal portions of the barrier surrounding the wound remain in fluid-tight sealing engagement with the skin, since the swelling of the central portion of the barrier has little tendency to induce separation of the barrier from the skin. The surrounding skin is effectively protected from wound fluid even though the dressing is used for extended time periods. Moreover, water-absorbency of the barrier layer can be safely increased by including more hydrocolloid as desired, and the increased swelling of the central portion of the barrier avoids creating irritating pressure against the surface of the wound.

The backing may be formed of a thin, stretchable foam material, such as foams formed from polyvinyl chloride or polyurethane. A closed cell foam may be used to provide a sealed backing, which protects the wound from the surrounding environment. However, by employing a partially open cell foam which is porous to the transmission of moisture vapor, the backing layer can cooperate with the barrier layer to, in effect, increase the fluid absorbing capacity of the barrier layer. Water absorbed into the barrier layer is transferred through the backing layer and evaporated into the atmosphere, thereby restoring and maintaining the fluid absorbing capacity of the barrier layer.

The relative "wet tack" and "dry tack" adherence of the barrier can be controlled or modified as required for optimized results. Tackifier polymers increasing dry tack can be included, thereby improving the seal between the barrier and the skin surrounding the wound without at the same time leading to wound irritation. The initial wet tack of the barrier and the elasticity of the backing permit the dressing to be formed into the wound on application. In preferred embodiments, however, when the barrier is saturated with water it has substantially no wet tack so that the swollen central portion separates easily and freely from the wound.

The foregoing features of the invention in combination provide a greatly improved system for management of pressure sores and ulcers. The wound dressings need to be changed less frequently because they can be designed to absorb larger amounts of exudate. Leaving the dressings on the wound longer does not result in increased skin irritation around the wound. The wound fluid is excluded from contact with the skin, even though the portion of the barrier over the wound has enlarged to many times its original volume. The stretchability of the backing tends not only to confine the forces generated by the swelling of the barrier to the area of the wound, but also tends to relieve undue pressure from being exerted on the wound area. As the central area of the dressing swells its diameter can be observed and used as an indicator for removing and replacing the barrier. Removal can be carried out easily and quickly, the barrier peeling off in one piece without irritation of the wound area due to adherence of the barrier, and the wound area is left clean and in condition for inspection.

THE DRAWINGS

A wound dressing embodying the present invention is shown in the accompanying drawings, in which—

FIG. 1 is a plan view of the wound dressing as applied to a dermal ulcer, part of the dressing being broken away to show its interior construction;

FIG. 2 is a side elevational view showing the dressing applied to the ulcer;

FIG. 3 is a fragmentary enlarged view of the dressing before application;

FIGS. 4, 5, and 6 are side elevational sectional views illustrating progressive swelling of the portion of the barrier over the ulcer; and FIG. 7 is a perspective view illustrating removal of the dressing from the ulcer.

DETAILED DESCRIPTION

The occlusive dressing of this invention preferably includes only two layers, a skin-contacting barrier layer and an overlying backing layer adhesively united thereto. For accomplishing the purpose of this invention, it is important that the backing sheet be formed of an elastic material which is stretchable under the pressure created by the swelling of the barrier material as it absorbs wound exudate. The required degree of stretchability can be determined by a standard test procedure, as will subsequently be described in detail. The operative criteria is that the sheet of elastic backing material should be stretchable at least to the extent that a 50% elongation without rupture is produced by a tensioning stress of not over 1.5 pounds per inch of width. In preferred embodiments, the 50% elongation as specified is obtained at a tensioning stress of less than 1.2 pounds, for example, at a tensioning stress of not over 1.0 pounds per inch of width, such as from 0.3 to 0.9 lbs/in. width.

Foam backings can be used which satisfy the foregoing criteria. But many commercially available plastic foams in sheet form do not have the required degree of elasticity. Particularly suitable sheet foams are available from the Norton Company, Granville, N.Y., being sold under the trademark "Sof-Med" Foams. These foams are made from polyvinyl chloride and are essentially closed cell foams, the closed cell content being over 90%. An excellent backing is the "Sof-Med" sheet foam "V-631" having a thickness of 1/32 inches (approximately 30 mils). Using the specified stretchability test, the "V-631" foam was found to elongate 50% per inch of width at around 0.9 pounds tensioning stress.

A partially open cell foam suitable for use in the wound care dressing of this invention is available from Semex Medical, Norristown, Pa. This is a polyurethane foam having a thickness of approximately 1/32", and a porosity of the order of 50%±10%. The foam is available in a range of densities from 12 to 20 lbs./cu. ft. For example, one standard product (MU2422-00) has a density of about 13.5 lbs./cu. ft. and is available in a 1/32" thickness at approximately a 50% porosity (50% open cell). In testing that backing for use in the present invention, it was found to have an especially advantageous stretchability criteria, elongating 50% per inch of width at 0.32 lbs. tensioning stress. This backing provides the further advantage that water from the wound fluid absorbed into the barrier layer is transferred through the porous backing and evaporated to the atmosphere. The fluid absorbing capacity of the barrier layer is therefore maintained and, in effect, increased beyond that which would be provided if the backing was non-porous.

Thin films may also be used as the backing layer, providing they exhibit the required degree of stretchability. For example, polyurethane, latex rubber or silicone films can be used. Such films can range in thickness from about 0.5 to 5.0 mils. In order to provide the desired degree of stretchability such films will usually have a thickness in the range of about 0.5 to 1.5 mils, such as about 1 mil. For example, the polyurethane film of 1 mil thickness was tested and found to have a 50% elongation per inch of width at a tensioning stress of about 0.7 pounds, whereas a latex film of 4 mil thickness was tested and found to have a 50% elongation per inch of width at a tensioning stress of about 0.3 pounds.

If an additional layer is included between the fluid absorbing barrier layer and the backing layer, the composite of the intermediate layer and the backing layer must meet the stretchability criteria set out above. It has therefore been found preferable to have the backing layer in direct contact with the barrier layer, and to utilize a backing of the kinds described above, viz. foam backings of 25 to 35 mils thickness, or film backings of 0.5 to 1.5 mil thickness.

Although highly stretchable film backings are commercially available and provide some of the advantages of the present invention, foam backings of the character described above are presently believed to be preferred. The foam backing may be either non-porous or porous, but where a partially-open cell, porous-type foam backing is employed, an additional method of functioning is provided.

The barrier layer is formulated from a mixture of elastomers and hydrocolloids. For example, polyisobutylene (PIB) may be employed as one elastomeric ingredient. However, since polyisobutylene cannot itself be chemically or physically cross-linked, it will be necessary to also include a cross-linking elastomeric resin. Cross-linkable resins which blend with polyisobutylene to form a continuous elastomeric phase are the copolymer resins formed from ethylene and vinyl acetate (EVA resins). Suitable formulations of EVA with PIB are disclosed in U.S. Pat. No. 4,477,325. As therein indicated, the proportions of ethylene to vinyl acetate may be varied. For the purposes of the present invention, from 40 to 60 parts of vinyl acetate may be copolymerized with from 60 to 40 parts by weight of ethylene. However, the exact proportions are not critical.

These EVA copolymers can be cross-linked by gamma irradiation. For example, a Cobalt-60 radiation source may be used to apply from 1.0 to 8.0 megarads. A desirable degree of cross-linking is obtainable with applied gamma irradiation of 2 to 4 megarads. For further details about such a cross-linking procedure, reference may be had to U.S. Pat. No. 4,477,325. Optionally, a minor amount of an additional cross-linking resin can be included, such as an acrylamide polymer which reacts with EVA to form cross-links. (See U.S. Pat. No. 4,477,325.) In the preferred formulations, the cross-linked network is formed essentially from the EVA polymer by irradiation of the EVA-containing elastomeric phase.

To provide for fluid absorption, the barrier material may contain a relatively high proportion of hydrocolloid, and also a super-absorbent type hydrocolloid. Super-absorbents can be formed from starch and acrylonitrile, the starch, either gelatinized or in granule form, being reacted with the acrylonitrile under alkaline conditions. For example, the resulting products may comprise a starch-polyacrylonitrile graft polymer, as described in U.S. Pat. Nos. 3,997,484 and 3,661,815. Synthetic super-absorbents may also be utilized, such as sodium polyacrylates.

The hydrocolloids which may be employed alone or in combination with the super-absorbent include pectin, carboxymethylcellulose, such as sodium CMC, karaya, gelatin, guar, etc. The hydrolloid mixture may include both natural vegetable hydrocolloid gums and synthetic hydrocolloids, for example, a mixture of pectin and sodium CMC has been found to be particularly suitable, especially when used in admixture with a super-absorbent such as sodium polyacrylate.

As a guide to formulating the barrier materials useful in the wound dressings of the present invention, the following general formula is set out:

| General Formula | |
|---|---|
| Ingredients | Parts by Weight |
| Polyisobutylene | 15 to 40 |
| Cross-linking elastomer | 5 to 25 |
| Hydrocolloids | 30 to 65 |

In combining the ingredients shown in the above formula, the hydrocolloid is dispersed in particulate form in a continuous elastomeric phase, including the polyisobutylene and the cross-linking elastomer. It is desirable to include sufficient water-absorbing hydrocolloids to provide the barrier layer with a water-absorbing capacity of from about 3 to 12 grams per gram of barrier. In preferred embodiments, the barrier provides a water absorbency of at least 4 grams per gram of barrier, such as a water absorbency in the range of 4 to 8 grams of water per gram of barrier. By the combination of hydrocolloids described above including a superabsorbent-type hydrocolloid, a high degree of water-absorbency can be obtained.

By way of further illustration, a preferred formula is set out below:

| Preferred Formula | |
|---|---|
| Ingredients | Parts by Weight |
| Polyisobutylene | 20 to 35 |
| EVA Copolymer Resin | 10 to 20 |
| Hydrocolloids[1] | 40 to 60 |
| Optional Ingredients[2] | 0 to 15 |

[1] May comprise a mixture of hydrocolloids (e.g., pectin and sodium carboxymethylcellulose) and a super-absorbent.
[2] May include a hydrocarbon tackifier and an oil extender and/or a resin cross-linking with EVA.

In the preferred formula, the EVA preferably contains from 40 to 60 percent by weight of vinyl acetate. In particular, copolymers containing approximately equal proportions of ethylene and vinyl acetate may be used. The dispersed particulate hydrocolloids may comprise a mixture of ordinary hydrocolloids and a super-absorbent hydrocolloid. For example, the hydrocolloids comprise pectin, sodium CMC, and sodium polyacrylate. The ordinary hydrocolloids, as distinguished from the super-absorbent type, may comprise from 30 to 50% by weight of the barrier, in admixture with from 5 to 15% by weight of a super-absorbent. These proportions can be adjusted to give the desired degree of fluid adsorbence.

The above preferred formula refers to optional ingredients. It may be desirable to include a tackifier resin for improving dry tack of the barrier layer. For example, hydrocarbon tackifiers may be used of the kind described in U.S. Pat. No. 4,231,369. The hydrocarbon tackifier may comprise a polymer or copolymer of dicyclopentadiene, alpha-pinene and beta-pinene. The amount of hydrocarbon tackifier is not critical, but if employed may be used in amounts of from 2 to 8 percent by weight of the barrier.

It may also be desirable, although not essential, to employ an oil extender material when it contains a hydrocarbon tackifier. Such oil extenders may include petrolatum, paraffin oil, polybutylene oil, vegetable oils, etc. In general, if an oil extender is employed, amounts ranging from 1 to 7 percent by weight of the barrier may be used.

In other embodiments, the elastomeric phase may be composed of or may contain as the cross-linking polymer such as a styrene-olefin-styrene block copolymer, or an ethylenepropylene block copolymer which is capable of forming physical cross-links, so that the elastomeric in solidified condition inherently provides a cross-linked network. Such physically cross-linking elastomeric polymers are described in U.S. Pat. No. 4,231,369.

In compounding formulas composed essentially of polyisobutylene (PIB), EVA copolymers, and hydrocolloids, the PIB and EVA can be first combined in a kneading-type mixer (or other suitable mixer) and mixed to substantial homogeneity. Mixing may then be continued with the slow addition of the hydrocolloids in powder form, which may be a preblended powder. Mixing is continued until a substantially homogeneous mixture is obtained in which the particulate hydrocolloids are dispersed in the continuous elastomer phase composed of the PIB and the EVA. The thus-prepared mixture may be formed into sheets of the desired thickness for the barrier layer by passing the material through a calendar having a pre-set gap, or the barrier sheets may be formed by compression in mold cavities of a desired depth. For purpose of the present invention, the exact thickness of the barrier layer is not critical. However, the preferred barrier layers will usually have a thickness in the range of about 30 to 90 mils, such as 40 to 70 mils. The barrier layer may be extruded onto a carrier sheet of releasable material, such as silicone-coated paper. The backing layer may be pressed into adhesive union with the top surface of the barrier layer, and the dressing assembly cut to the desired sizes by die-cutting. At the time of use, the release sheet is removed from the dressing, and the barrier layer applied over the wound area.

Where the barrier contains EVA or other resin cross-linking by irradiation, the barrier is irradiated after the dressing has been formed, either before or after packaging. The gamma irradiation will also serve to sterilize the dressing. It is therefore convenient to enclose the dressings in flexible wrappers for packaging of the dressing, and then to irradiate the packaged dressing to cross-link the barrier layer.

DESCRIPTION OF DRAWINGS

The construction and operation of wound dressings prepared in accordance with this invention are further illustrated by the accompanying drawings.

The dressing D includes the stretchable backing 10 which overlies the fluid-absorbing barrier layer 11. In FIG. 1 the lower right hand corner of the backing and the barrier layers are broken away. The borders of the dressing which are outside of the ulcer, as shown more clearly in FIG. 2, are adhesively united to the skin. On initial application, the dressing may be pressed gently into the ulcer area, extending through the epidermis into the dermis. The "dotting" of the barrier layer indicates dispersed particles of hydrocolloids, comprising a particulate solid phase within the continuous elastomeric phase.

In FIG. 3, protective paper 12, such as a silicone-coated paper, is shown being removed from the underside of the barrier layer, as would be done prior to the application of the dressing.

As illustrated in FIG. 2, fluid exuded by the ulcer U will be absorbed by the central portion of the barrier material overlying the dressing, the hydrocolloid particles swelling as they absorb the aqueous fluid. After a day or two of such swelling enlargement, the applied dressing may appear as shown in the cross-sectional view of FIG. 4. The enlarged central portion of the barrier 11a has stretched the central portion 10b of the backing upwardly into a domed configuration. As the absorption proceeds, after another day or two, the swelling of the central portion 11a may appear as shown in the cross-sectional view of FIG. 5. The swollen portion of the barrier 11a has stretched the central portion of the backing barrier 10b upwardly further permitting continued swelling of the barrier layer over the ulcer. As shown in FIG. 5, the swollen portion 11a has nearly reached the outer margins of the ulcer U.

Figure 1:
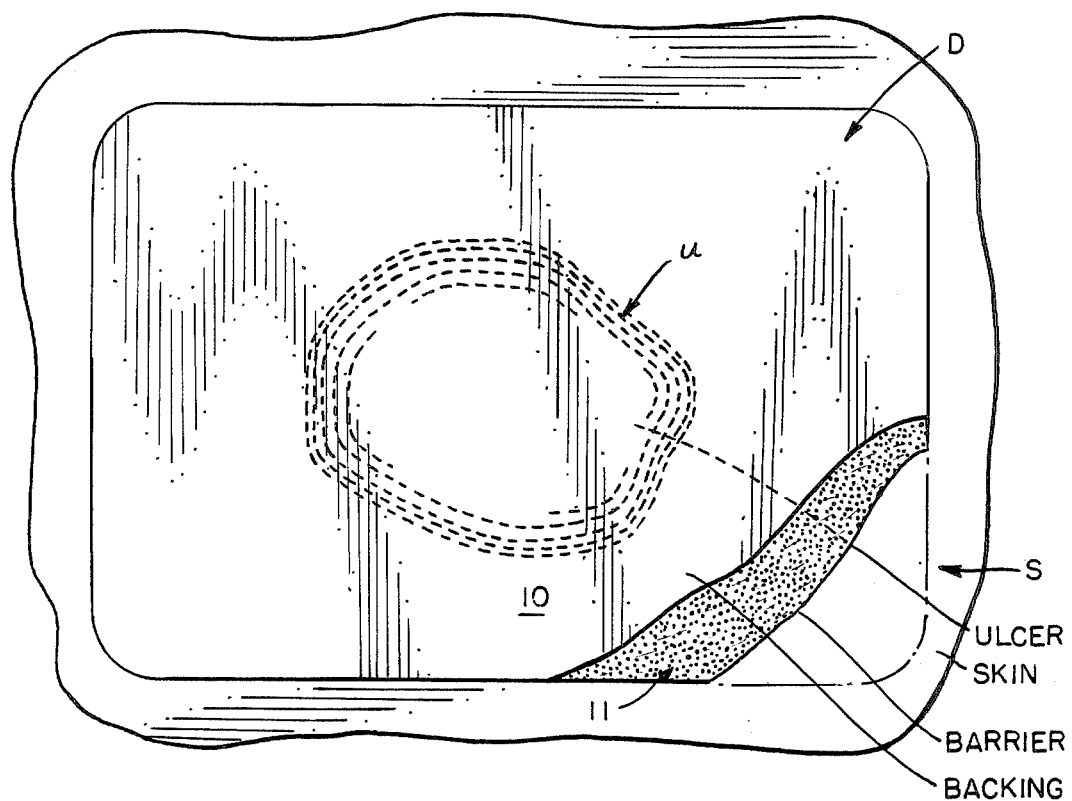
Referring to FIGS. 1 and 2, the wound dressing D is illustrated applied over a dermal ulcer U surrounded by skin S. The dotted lines around the ulcer U suggest an irregular margin of the ulcer area. Several descriptive labels have been applied in FIGS. 1 and 2.
Figure 2:
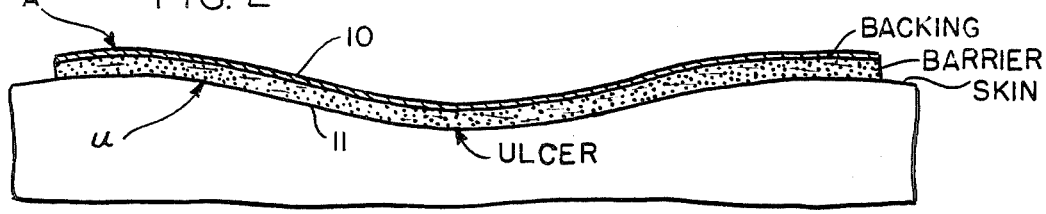
Figure 3:
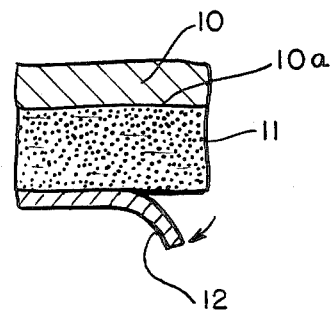
FIG. 3 shows an enlarged sectional view of a cross-section of the dressing barrier. The backing layer 10 may be adhesively united to the barrier layer 11 through the dry tack action of the elastomeric phase, or, if desired, the backing may have a pressure-sensitive adhesive on the surface 10a, which is to be attached to the barrier layer 11. Backing sheets suitable for use in forming the dressings of the present invention can be obtained with pressure-sensitive adhesives on one surface thereof.
Figure 4:
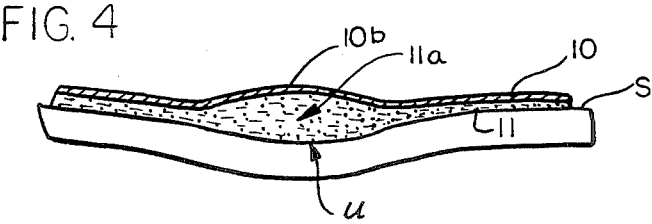
FIGS. 4 to 7 illustrate the way in which the wound dressing of this invention will function after application to an ulcer or other fluid-exuding skin wound.
Figure 5:
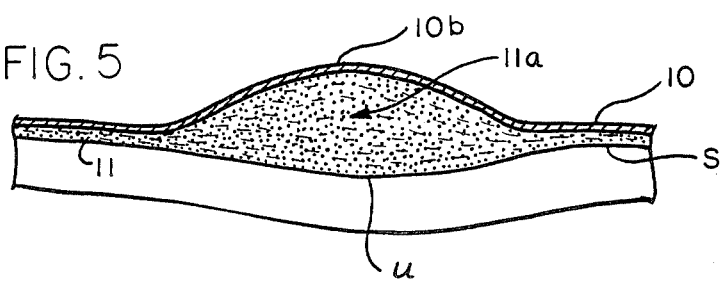
Figure 6:
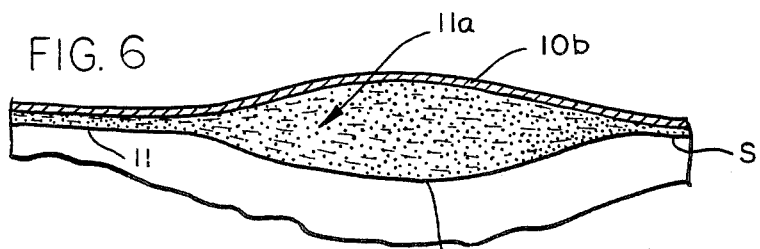

When the swollen area 11a begins to expand beyond the margins of the ulcer U, as shown in FIG. 6, it will usually be desirable to remove and replace the dressing. By observing the extent of swelling of the dressing in relation to the ulcer size, the removal stage can be visually determined.

Figure 7:
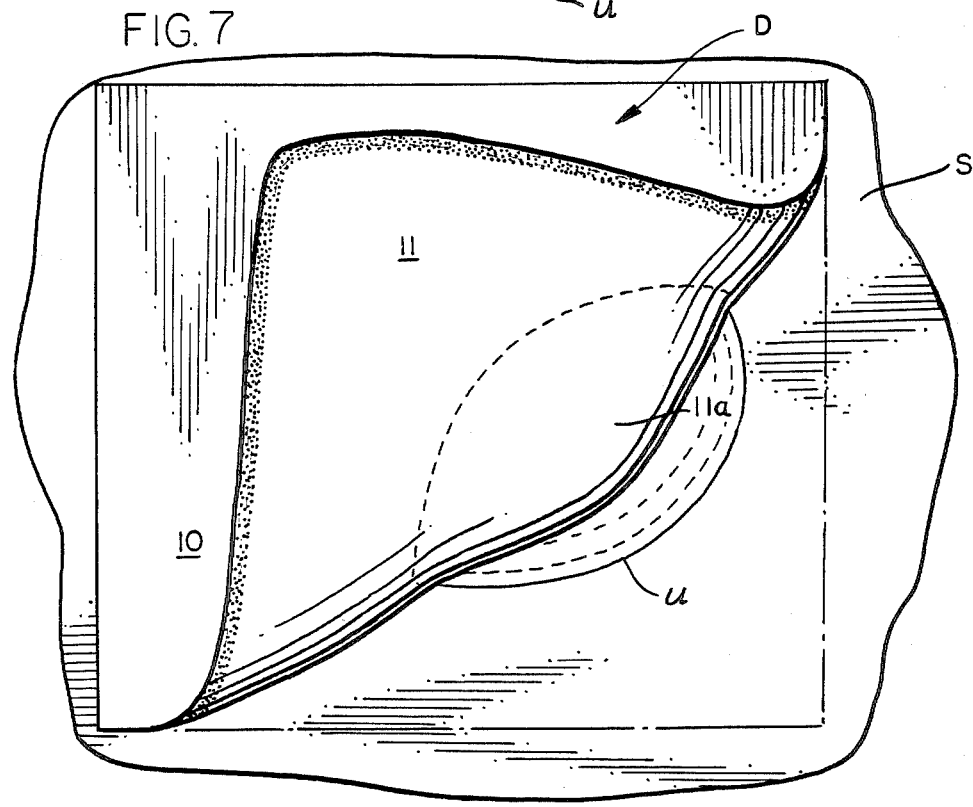

Removal of the dressing is illustrated in FIG. 7. The barrier layer although centrally swollen and saturated with wound fluid will remain integrated so that the entire dressing can be removed in one piece. FIG. 7 illustrates one side of the dressing being rolled back, and shows the swollen portion 11 as removed from the ulcer U.

The wound dressings of this invention are further illustrated by the following examples.

EXAMPLE I

One preferred example of a wound dressing for use in practicing the present invention employs a barrier material prepared according to the following Formula A.

| Formula A | |
|---|---|
| Ingredients | Weight Percent |
| Polyisobutylene[5] | 25 |
| 51% EVA[1] | 15 |
| Super absorber[2] | 10 |
| Pectin | 13 |
| CMC[3] | 28 |
| Polyalicyclic resin[4] | 5 |
| Petrolatum | 4 |
| | 100% |

[1] Copolymer of 49% ethylene/51% vinyl acetate.
[2] Starch sodium polyacrylate polymer.
[3] Sodium salt of carboxymethyl cellulose.
[4] Fully hydrogenated polyalicyclic hydrocarbon resin.
[5] Vistanex LM-MH.

The ingredients of Formula A can be compounded as follows:

The hydrocolloids can be first dry blended to form a dry mix for later addition to the other ingredients. The polyisobutylene, EVA and about 60% of the preblended hydrocolloid mix are combined in a kneading-type mixer (or other suitable mixer) and are mixed at 55° C. for five minutes after the EVA pellets begin to melt. The rest of the hydrocolloid premix, super absorber, tackifier resin and petrolatum are then added and mixing continues for another ten minutes until a substantially homogeneous final mixture is obtained.

The thus prepared mixture can be formed into the desired shape by any number of means commonly used for converting plastics and elastomers to such shapes. These means include compression molding and injection molding. Calendering and extrusion of the mixture in sheet form followed by die cutting into the desired shape may also be used. The currently preferred mode of preparation consists of extruding a ribbon of the desired width and thickness directly onto release paper. This ribbon can be covered on the exposed side with one of several types of backings, either porous or nonporous films being used.

This backing can be applied by hand or in conjunction with a compression roller on the production line.

After uniting the barrier layer to the backing layer, the assembly is cut into desired sizes for the wound dressings, such as 4"×4" wafers, 8"×8" wafers, and 8"×12" wafers, or any other desirable shape. The completed dressings are packaged in a heat sealed plastic bag. Following packaging, the dressings are irradiated at 2.5 Mrad of gamma radiation. The irradiation converts the EVA to a cross-linked network which effectively integrates the barrier layer, and the irradiation also sterilizes the packaged dressings.

Suitable backing layers for use in forming the dressings comprise:

(1) The "Sof-Med V-631" closed cell polyvinyl chloride foam (1/32 in gauge) of Norton Company, Granville, N.Y.;
(2) MU2422-00 polyurethane foam (1/32 in gauge, 50% porous) of Semex Medical, Norristown, Pa.;
(3) The polyether polyurethane film (1 mil thickness) obtained from General Foam Corporation, Paramus, N.J.; and
(4) The latex rubber film (4 mil thickness) obtained from Hygenic Corporation, Akron, Ohio.

Samples of these backing materials were tested by pulling 1"×6" test strips on an "Instron" testing machine. The value of tensioning force necessary to stretch each sample by 50% was then recorded, and an average value determined. The following backing materials were selected as suitable for use in producing this invention with respect to their stretchability.

| Test Samples | Average Tensioning Force at 50% Elongation (lbs.) |
|---|---|
| 1/32" Sof-Med PVC foam | 0.94 |
| 1/32" Semex polyurethane foam | 0.32 |
| 1.0 mil polyurethane film | 0.85 |
| 4 mil natural rubber latex film | 0.25 |

All of the above materials, with the exception of the Semex polyurethane foam, provide essentially sealed backing layers. By using the Semex foam, which is a partially open-cell foam, a backing layer is provided which has sufficient porosity to permit water vapor to be transferred therethrough from the barrier layer. This combination provides a special cooperative action.

During periods in which large amounts of wound fluid are being discharged, the barrier layer can absorb the fluid, enlarging in size, and stretching the backing layer. As the amount of wound discharge decreases, transmission of moisture through the backing layer to the atmosphere reduces the amount of fluid retained in the barrier layer, permitting it to contract in size with reduction in the amount of stretch in the backing layer. In this manner, large and variable amounts of wound fluid can be accommodated. The wound dressing continues to be effective at all times.

EXAMPLES 2 TO 12

Following the procedure of Example 1 other dressings within the scope of this invention can be prepared as summarized below. The ingredient identifications correspond with those of Formula A. The gelatin and fumed silica are optional additional ingredients. Example 2 is a formulation for decreased absorption (1.5 g water/1 g barrier) while Example 12 is a formulation for increasing absorption (10 g water/1 g barrier). The other examples indicate permissible variations within the broad concept of the invention. The barrier formulations of Examples 2 to 12 can be used with the backings described in Example 1, being formed and assembled as described therein to provide the complete occlusive dressings. Preferred backings are the closed cell polyvinyl chloride foam (Sof-Med V-631), or the partially open cell polyurethane foam (Semex MU2422-00). The respective advantages of these combinations are as described above.

| Ingredients (wt. %) | EXAMPLE NOS. | | | | | | | | | | |
|---|---|---|---|---|---|---|---|---|---|---|---|
| | 2 | 3 | 4 | 5 | 6 | 7 | 8 | 9 | 10 | 11 | 12 |
| Polyisobutylene | 23 | 19 | 25 | 25 | 25 | 25 | 20 | 20 | 20 | 30 | 20 |
| 51% EVA | 15 | 15 | 15 | 13 | 10 | 15 | 20 | 10 | 20 | 20 | 10 |
| Super absorber | 10 | 10 | 10 | 15 | 15 | 20 | 20 | 20 | 25 | | 25 |
| Pectin | 11 | 11 | 13 | 11 | 16 | 11 | 11 | 16 | 11 | 10.3 | 11 |
| CMC | 9 | 9 | 21 | 26 | 26 | 21 | 21 | 26 | 16 | 8.4 | 26 |
| Polyalicyclic resin | 12 | 12 | 10 | 5 | 5 | 5 | 5 | 5 | 5 | 17.0 | 5 |
| Petrolatum | 3 | 4 | 6 | 5 | 3 | 3 | 3 | 3 | 3 | 3 | 3 |
| Gelatin | 17 | 17 | | | | | | | | 8.3 | |
| Fumed silica | | 3 | | | | | | | | 3 | |

We claim:

1. An occlusive dressing for care of skin wounds, which includes a skin contacting barrier layer and an overlying backing layer adhesively united thereto; said backing layer being formed from a thin sheet which is stretchable to the extent that a 50% elongation without rupture is produced by a tensioning stress of not over 1.5 pounds per inch of width, said barrier layer being formed from a composition composed essentially of:
   (a) an elastomeric phase integrated by a cross-linked polymer network; and
   (b) a particulate water-absorbing hydrocolloid phase dispersed in said cross-linked elastomeric phase, sufficient hydrocolloid being present to provide said barrier layer with a water absorbing capacity of from 3 to 12 grams per gram of barrier, said barrier layer swelling progressively as it absorbs aqueous fluid while remaining integrated and when saturated having substantially no adherence to the skin, whereby the portion of said barrier layer over the wound enlarges by stretching the backing sheet as it absorbs wound exudate and thereafter is removable in one piece with minimal irritation of the wound area.

2. The occlusive dressing of claim 1 in which said barrier layer contains an elastomeric copolymer of ethylene and vinyl acetate which has been cross-linked by gamma irradiation to provide said polymer network.

3. The occlusive dressing of claim 1 in which said backing layer is a foam material which is stretchable to the extent that a 50% elongation without rupture is produced by a tensioning stress of not over 1.0 pounds per inch of width.

4. An occlusive dressing for care of skin wounds, which includes a skin-contacting barrier layer and an overlying backing layer adhesively united thereto, said backing layer being formed from a thin sheet which is stretchable to the extent that a 50% elongation without rupture is produced by a tensioning stress of not over 1.2 pounds per inch of width, said barrier layer being formed from a composition composed essentially of:

(a) an elastomeric phase integrated by a cross-linked polymer network; and (b) a particulate water-absorbing hydrocolloid phase dispersed in said cross-linked elastomeric phase, sufficient hydrocolloid being present to provide said barrier layer with a water absorbing capacity of from 4 to 8 grams per gram of barrier, said barrier layer swelling progressively as it absorbs aqueous fluid while remaining integrated and when saturated having substantially no adherence to the skin, whereby the portion of said barrier layer over the wound enlarges by stretching the backing sheet as it absorbs wound exudate and thereafter is removable in one piece with minimal irritation of the wound area.

5. The occlusive dressing of claim 3 in which the elastomeric phase of said barrier layer is primarily of a mixture of polyisobutylene (PIB) and said EVA copolymer.

6. The occlusive dressing of claim 3 in which said backing layer is an essentially closed cell foam material which is stretchable to the extent that a 50% elongation without rupture is produced by a tensioning stress of not over 1.0 pounds per inch of width.

7. The occlusive dressing of claim 3 in which said backing layer is a partially open cell foam material which permits the transmission of water vapor therethrough and which is stretchable to the extent that a 50% elongation without rupture is produced by a tensioning stress not over 1.0 pounds per inch of width.

8. An occlusive dressing for care of skin wounds, which includes a skin-contacting barrier layer and an overlying backing layer adhesively united thereto, said backing layer being formed from a thin sheet which is stretchable to the extent that a 50% elongation without rupture is produced by a tensioning stress of not over 1.0 pounds per inch of width, said barrier layer being formed from a composition composed essentially of:

(a) an elastomeric phase composed primarily of a mixture of polyisobutylene (PIB) and a copolymer of ethylene and vinyl acetate (EVA) from 0.2 to 0.8 parts of said EVA being present per part of said PIB, said EVA having been cross-linked by gamma irradiation; and (b) a particulate water-absorbing hydrocolloid phase dispersed in said elastomeric phase, sufficient hydrocolloid being present to provide said barrier layer with a water absorbing capacity of from 4 to 8 grams of water per gram of barrier, said barrier layer swelling progressively as it absorbs aqueous fluid while remaining integrated up to saturation and having substantially no wet tack at saturation, whereby the portion of said barrier layer over the wound enlarges by stretching the backing sheet as it absorbs wound exudate, and when saturated is removable in one piece with minimal irritation of the wound area.

9. The occlusive dressing of claim 8 in which said backing layer is a closed cell polyvinyl chloride foam having a thickness of from 25 to 35 mils.

10. The occlusive dressing of claim 8 in which said backing layer is a partially open cell polyurethane foam having a thickness of from 25 to 35 mils, said foam backing layer permitting the transmission of water vapor therethrough.

11. The occlusive dressing of claim 6 in which said backing sheet is a polyurethane film having a thickness of from 0.5 to 1.5 mils.

12. The occlusive dressing of claim 7 in which said backing sheet is a latex rubber film having a thickness of 2 to 15 mils.

* * * * *